United States Patent [19]

Kronholm et al.

[11] Patent Number: 5,252,559

[45] Date of Patent: Oct. 12, 1993

[54] HIS-GLY-GLY PEPTIDE AND DERIVATIVES THEREOF FOR HAIR GROWTH

[75] Inventors: Kurt G. Kronholm, Oxford; Richard J. Schwen, Cincinnati; Mark R. Sine, Morrow; Raphael Warren; Cynthia J. Wawrzyniak, both of Cincinnati, all of Ohio

[73] Assignee: The Procter & Gamble Company, Cincinnati, Ohio

[21] Appl. No.: 747,811

[22] Filed: Aug. 20, 1991

[51] Int. Cl.$^5$ .................... A61K 37/02; C07K 5/08
[52] U.S. Cl. .......................................... 514/18; 530/331
[58] Field of Search ...................... 514/18; 530/331

[56] References Cited

U.S. PATENT DOCUMENTS

| | | | |
|---|---|---|---|
| 4,665,054 | 5/1987 | Pickart | 514/18 |
| 4,760,051 | 7/1988 | Pickart | 514/6 |

FOREIGN PATENT DOCUMENTS

| | | |
|---|---|---|
| 0415598A1 | 3/1991 | European Pat. Off. . |
| 0422765A1 | 4/1991 | European Pat. Off. . |
| 88/08695 | 11/1988 | World Int. Prop. O. . |

OTHER PUBLICATIONS

Bachem Bioscience, Inc., Catalog US 4—1991 p. 295.
Ueda, J., A., Hanaki, N. Yoshida and T. Nakajima—"$^1$H-Nuclear Magnetic Resonance Study of the Interaction of Zinc(II) Ion with a Histidine-Containing Peptide, L-Histidylglycylglycine," Chem. Pharm. Bull. vol. 33, pp. 3096–3100 (1985).
Yokoyama, A., H. Aiba and H. Tanaka—"Acid Dissociation Constants of Some Histidine-Containing Peptides and Formation Constants of Thier Metal Complexes," Bulletin of the Chemical Society of Japan, vol. 47, pp. 112–117 (1974).
Schneider, F.—"Tripeptide des Histidins," Z. Physiol. Chem., vol. 321, pp. 38–48 (1960).
Davis, N. C.—"Action of Proteolytic Enzymes on Some Peptides and Derivatives Containing Histidine," J. Bio. Chem., vol. 223, pp. 935–947 (1956).

*Primary Examiner*—Lester L. Lee
*Attorney, Agent, or Firm*—Brahm J. Corstanje; Milton B. Graff, IV; Jerry J. Yetter

[57] ABSTRACT

The present invention relates to a composition for regulating hair growth comprising a safe and effective amount of the tripeptide histidyl-glycyl-glycine, or a derivative thereof, and a pharmaceutically-acceptable carrier.

7 Claims, No Drawings

HIS-GLY-GLY PEPTIDE AND DERIVATIVES THEREOF FOR HAIR GROWTH

TECHNICAL FIELD

The Present Invention relates to novel compositions which regulate hair growth.

BACKGROUND OF INVENTION

Society in general continues to attach a stigma to hair loss. The desire for a healthy full head of hair has resulted in a variety of approaches to the "curing" of baldness. Some of these approaches include the following:

U.S. Pat. No. 4,139,619, Chidsey, assigned to the Upjohn Company, issued Feb. 13, 1979, discloses a topical composition comprising Minoxidil and related iminopyrimidines which stimulates the conversion of vellus hair to terminal hair and increases the rate of growth of terminal hair.

U.S. Pat. No. 4,832,946, Green, assigned to Unilever, issued May 23, 1989, discloses a composition for topical application to mammalian hair or skin, comprising an amount of the cell-free supernatant from a culture of dermal papilla fibroblasts which increases hair growth in the rat by at least 10% more than that of a control composition.

World Patent Application 88/08695, Pickart, assigned to ProCyte Corporation, published Nov. 17, 1988, discloses a composition comprising a derivative of the peptide/copper complex glycyl-L-histidyl-L-lysine:copper(II) for use in the stimulation of hair growth.

OBJECTS OF THE PRESENT INVENTION

It is an object of the present invention to provide compositions for regulating hair growth.

It is also an object of the present invention to provide methods for regulating hair growth which comprise administration of such compositions for regulating hair growth.

SUMMARY OF THE INVENTION

The present invention relates to a composition for regulating hair growth comprising a safe and effective amount of the tripeptide histidyl-glycyl-glycine or a derivative thereof having the formula:

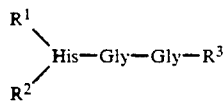

wherein $-R^1$ is selected from the group consisting of $-H$, alkylcarbonyl, arylcarbonyl, arylalkylcarbonyl, alkyloxycarbonyl, alkyl, aryl and arylalkyl; $-R^2$ is selected from the group consisting of $-H$, alkylcarbonyl, arylcarbonyl, arylalkylcarbonyl, alkoxycarbonyl, alkyl, aryl and arylalkyl; and $-R^3$ is selected from the group consisting of $-OH$, alkoxy, aryloxy, arylalkyloxy and $-O^-M^+$ wherein $M^+$ is a cation; and wherein $-R^1$ is bound to the α nitrogen of His, $-R^2$ is bound to the imidazole nitrogen of His, and $-R^3$ is bound to the carbonyl moiety of Gly; and a pharmaceutically-acceptable topical carrier.

The present invention also relates to methods of using such compositions for regulating hair growth.

DETAILED DESCRIPTION OF THE INVENTION

As used herein, "alkyl" means a carbon-containing chain which may be straight or branched, preferably straight; substituted (mono- or poly-) or unsubstituted, preferably unsubstituted; saturated, monounsaturated (i.e., one double or triple bond in the chain), or polyunsaturated (i.e., two or more double bonds in the chain; two or more triple bonds in the chain; one or more double and one or more triple bonds in the chain), preferably saturated. Preferably the alkyl has from about 1 to about 12 carbon atoms in the chain, more preferably from about 1 to about 8, more preferably still from about 1 to about 4.

As used herein, "aryl" means an aromatic; substituted (mono- or poly-) or unsubstituted, preferably unsubstituted. Preferred aryls are phenyl, pyridyl, pyrimidyl and napthyl; more preferred is phenyl.

As used herein, the term "substituted" means mono- or poly-substituted; preferably mono-, di- or trisubstituted. Examples of substituents include halogen (i.e., chlorine, bromine, fluorine and iodine), hydroxy, alkoxy (preferably methoxy, ethoxy and tert-butyloxy), aryloxy (preferably pheroxy), amino, alkylamino (preferably methylamino, ethylamino and isopropylamino), dialkylamino (preferably dimethylamino, diethylamino and diisopropylamino), acyloxy (preferably acetoxy and benzoyloxy), thio, alkylthio (preferably methylthio and ethylthio), cyano and nitro.

As used herein, "arylalkyl" means $R'-R''-$, wherein $R'$ is an aryl and $R''$ is an alkyl.

As used herein, "alkylcarbonyl" means

wherein $R''$ is an alkyl.

As used herein, "arylcarbonyl" means

wherein $R'$ is an aryl.

As used herein, "arylalkylcarbonyl" means

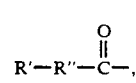

wherein $R'$ is an aryl and $R''$ is an alkyl.

As used herein, "alkyloxycarbonyl" means

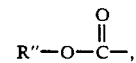

wherein $R''$ is an alkyl.

As used herein, "alkoxy" means $R''-O-$, wherein $R''$ is an alkyl.

As used herein, "aryloxy" means $R'-O-$, wherein $R'$ is an aryl.

As used herein, "arylalkyloxy" means $R'-R''-O-$, wherein $R'$ is an aryl and $R''$ is an alkyl.

As used herein, $$\begin{array}{c} R^1 \\ \diagdown \\ \phantom{R^2}\diagup \mathrm{His{-}Gly{-}Gly{-}R^3} \text{ means} \\ R^2 \end{array}$$

$$R^1{-}NH{-}\underset{\underset{\underset{\underset{R^2{-}N}{\diagup}}{CH_2}}{CH_2}}{\overset{\overset{O}{\|}}{CH}}{-}C{-}NH{-}CH_2{-}\overset{\overset{O}{\|}}{C}{-}NH{-}CH_2{-}\overset{\overset{O}{\|}}{C}{-}R^3$$

As used herein, "His-Gly-Gly" means the tripeptide histidyl-glycyl-glycine.

As used herein, "topical application" means directly laying on or spreading on outer skin.

As used herein, "cutaneous injection" means introduction of a substance beneath or within the skin by a hypodermic needle.

As used herein, "safe and effective amount" means a sufficient amount of a composition to provide a desired hair growth regulating effect at a reasonable benefit/risk ratio.

As used herein, "pharmaceutically-acceptable" means that drugs, medicaments or inert ingredients which the term describes are suitable for use in contact with the tissues of humans and lower animals without undue toxicity, incompatibility, instability, irritation, allergic, response, and the like, commensurate with a reason sable benefit/risk ratio.

As used herein, "regulating hair growth" means inducing the formation of a greater number of hair strands, and/or increasing the diameter of the hair strand, and/or lengthening the hair strand, and/or changing the hair follicle from vellus to terminal, and/or preventing, retarding, or arresting the process of hair loss.

As used herein, "vellus hair follicle" means a hair follicle which produces a soft, short, and often colorless hair fiber. The size of the vellus follicle is considerably smaller than the terminal hair follicle. In an adult, vellus follicles can be found on the forehead, eyelids, and bald scalp.

As used herein, "terminal follicle" means a hair follicle which produces a coarse, long, and often pigmented hair follicle. The size of the terminal follicle is considerably larger than the vellus follicle. In the adult, terminal follicles can be found on the scalp, axilla and pubic areas.

Active Agents

As used herein, "hair growth peptide" means the peptide Histidyl-glycyl-glycine or a derivative thereof having the general formula:

$$\begin{array}{c} R^1 \\ \diagdown \\ \phantom{R^2}\diagup \mathrm{His{-}Gly{-}Gly{-}R^3} \\ R^2 \end{array}$$

$R^1$ is selected from the group consisting of —H, alkylcarbonyl, arylcarbonyl, arylalkylcarbonyl, alkoxycarbonyl, alkyl, aryl and arylalkyl; preferably —H, alkylcarbonyl and alkoxycarbonyl; more preferably —H.

$R^2$ is selected from the group consisting of —H, alkylcarbonyl, arylcarbonyl, arylalkylcarbonyl, alkoxycarbonyl, alkyl, aryl and arylalkyl; preferably —H, alkylcarbonyl and alkoxycarbonyl; more preferably —H.

$R^3$ is selected from the group consisting of —OH, alkoxy, aryloxy, arylalkyloxy and —O$^-$M$^+$ wherein M$^+$ is a cation; preferably —OH and alkoxy; more preferably —OH.

Preferably M$^+$ is selected from the group consisting of Na$^+$, K$^+$, (Ca$^{++}$)$_{\frac{1}{2}}$, (Mg$^{++}$)$_{\frac{1}{2}}$ and (Mn$^{++}$)$_{\frac{1}{2}}$; more preferably Na$^+$ and K$^+$.

The examples contained herein further describe and demonstrate preferred embodiments within the scope of the present invention. The examples are given solely for the purpose of illustration, and are not to be construed as limitations of the present invention since many variations thereof are possible without departing from its spirit and scope.

Synthesis of the Active Agents

Example I

Histidyl-glycyl-glycine Preparation

Histidyl-glycyl-glycine has the formula $$\begin{array}{c} R^1 \\ \diagdown \\ \phantom{R^2}\diagup \mathrm{His{-}Gly{-}Gly{-}R^3} \\ R^2 \end{array}$$

as defined supra, wherein —R$^1$ and —R$^2$ are each —H and —R$^3$ is —OH, and may be obtained from Bachem Bioscience Inc. (Philadelphia, Pa.) or synthesized as follows:

A 10-20% excess of N-t-butyloxycarbonyl-L-glycine (BOC-Gly-OH) is coupled to glycyl t-butyl ester (H-Gly-TBE) with dicyclohexylcarbodiimide (DCC) in dichloromethane for one hour. The solution is filtered and the solvent is removed on a rotary evaporator. The residue is taken up in ethyl acetate and washed successively with 1M KHSO$_4$, water, saturated NaHCO$_3$ solution, and water. The ethyl acetate solution is dried over MgSO$_4$, filtered, and the solvent is removed on a rotary evaporator to form Boc-Gly-Gly-TBE as a semi-solid oil.

Removal of the BOC group is performed with 4N HCL/dioxane at room temperature (RT) for 30-40 minutes. Dioxane is removed by rotary evaporator and the residue is taken up in ethyl acetate. The solution is washed with saturated NaHCO$_3$ solution, filtered and quickly dried for the next coupling.

A 10-20% excess of Nα-t-butyloxycarbonyl-N(im)-tosyl-L-histidine-(BOC-His(Tos)-OH) is coupled to the H-Gly-Gly-TBE with DCC in dichloromethane for one hour. The solution is filtered and the solvent is removed on a rotary evaporator. The residue is taken up in ethyl acetate and washed successively with 1M KHSO$_4$, water, saturated NaHCO$_3$ solution, and water. The ethyl acetate solution is dried over MgSO$_4$, filtered, and the solvent is removed on a rotary evaporator to form BOC-His(Tos)-Gly-Gly-TBE.

The protecting groups are removed by hydrogen fluoride (HF) cleavage with 95% HF and 5% anisole at 0° C. for 60 minutes. The histidyl-glycyl-glycine is purified by preparative scale reverse phase high pressure liquid chromatography (HPLC).

Example II

Histidyl-glycyl-glycine n-octyl ester Preparation

Histidyl-glycyl-glycine n-octyl ester has the formula

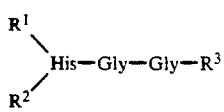

as defined supra, wherein —R¹ is —H, —R² is —H and —R³ is —O—(CH₂)₇CH₃. The compound is synthesized as follows:

A mixture of H-Gly-OH, n-octanol, and p-toluenesulfonic acid monohydrate in benzene is refluxed overnight in a Dean-Stark trap to remove water. After cooling, dry ethyl ether is added. The solution is then allowed to precipitate at 0° C. overnight. The precipitated solid is added to 50 mL of 1M K₂CO₃ and 50 mL of dichloromethane. After extraction, the layers are separated and the organic phase washed with water and brine, then dried with anhydrous MgSO₄. The solution is filtered and H-Gly-n-octyl ester is purified by flash column chromatography.

The remainder of the preparation is the same as for Histidyl-glycyl-glycine except H-Gly-n-octyl ester is substituted for H-Gly-TBE in Example I.

Example III

Histidyl-glycyl-glycine benzyl ester Preparation

Histidyl-glycyl-glycine benzyl ester has the formula

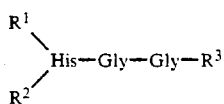

as defined supra, wherein —R¹ is —H, —R² is —H and —R³ is

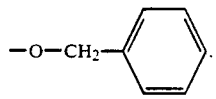

The compound is synthesized as follows:

A 10-20% excess of BOC-Gly-OH is coupled to the H-Gly-O-Bzl with DCC in dichloromethane for one hour. The solution is filtered and the solvent is removed on a rotary evaporator. The residue is taken up in ethyl acetate and washed successively with 1M KHSO₄, water, saturated NaHCO₃ solution, and water. The ethyl acetate solution is dried over MgSO₄, filtered, and the solvent is removed on a rotary evaporator to form BOC-Gly-Gly-O-Bzl as a semisolid oil.

Removal of the BOC group is performed with 4N HCL/dioxane at RT for 30-40 minutes. Dioxane is removed by rotary evaporator and the residue is taken up in ethyl acetate. The solution is washed with saturated NaHCO₃ solution, filtered and quickly dried for the next coupling.

A 10-20% excess of Nα-t-butyloxycarbonyl-N-(im)-triphenylmethylhistidine (BOC-His(Trt)-OH) is coupled to H-Gly-Gly-O-Bzl with DCC in dichloromethane for one hour. The solution is filtered and the solvent is removed on a rotary evaporator. The residue is taken up in ethyl acetate and washed successively with 1M KHSO₄, water, saturated NaHCO₃ solution, and water. The ethyl acetate solution is dried over MgSO₄, filtered, and the solvent is removed on a rotary evaporator to form BOC-His(Trt)-Gly-Gly-O-Bzl as a semisolid oil.

The protecting groups are removed by trifluoroacetic acid (TFA) cleavage with 90% TFA, 5% thioanisole, 3% ethanethiol, 2% anisole at 0° C. for 60 minutes. The Histidyl-glycyl-glycine benzyl ether is purified by preparative scale reverse phase HPLC.

Example IV

N-Histidyl-glycyl-glycyl n-octyl amide Preparation

N-Histdy-glycyl-glycyl n-octyl amide has the formula

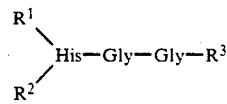

as defined supra, wherein —R¹ is

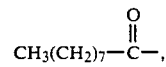

—R² is —H and —R³ is —OH. The compound is synthesized as follows:

BOC-His(Tos)-Gly-Gly-TBE is prepared as above in the histydyl-glycyl-glycine preparation. Removal of the BOC group is performed with 4N HCL/dioxane at room temperature of 30-40 minutes. Dioxane is removed by rotary evaporator and the residue is taken up in ethyl acetate. The solution is washed with saturated NaHCO₃ solution, filtered and quickly dried for the next coupling.

A 10-20% excess of n-octanoic acid is coupled to H-His(Tos)-Gly-Gly-TBE with DCC in dichloromethane for one hour. The solution is filtered and the solvent is removed on a rotary evaporator. The residue is taken up in ethyl acetate and washed successively with 1M KHSO₄, water, saturated NaHCO₃ solution, and water. The ethyl acetate solution is dried over MgSO₄, filtered, and the solvent is removed on a rotary evaporator to form a semisolid oil.

The protecting groups are removed by HF cleavage with 95% HF and 5% anisole at 0° C. for 60 minutes. The N-histidyl-glycyl-glycyl n-octyl amide is purified by preparative scale reverse phase HPLC.

Example V

Nα-t-butyloxycarbonyl-Histidyl-glycyl-glycine Preparation

Nα-t-butyloxycarbonyl-Histidyl-glycyl-glycine has the formula

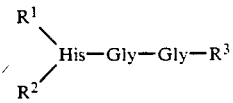

as defined supra, wherein —R¹ is

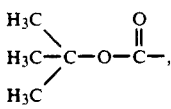

—$R^2$ is —H and —$R^3$ is —OH. The compound is synthesized as follows:

Phosgene (20% in toluene) is added to a solution of octanol and triethylamine in toluene at 0° C., then stirred at room temperature for 3 hours. This solution is then slowly added to a solution of His-Gly-Gly (1 equivalent) and triethylamine in toluene and allowed to stir for 2 hours. The volatiles are removed on a rotary evaporator and the residue is taken up in ethyl acetate and washed successively with 1M KHSO$_4$, water, saturated NaHCO$_3$ solution, and water. The ethyl acetate solution is dried over MgSO$_4$, filtered, and the solvent is removed on a rotary evaporator to form Nα-octyloxycarbonyl-His-Gly-Gly as a semisolid oil.

Example VI

N-(im)-octyloxycarbonyl-Histidyl-glycyl-glycine Preparation

N-(im)octyloxycarbonyl-Histidyl-glycyl-glycine has the formula

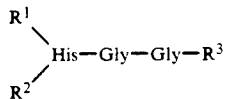

as defined supra, wherein —$R^1$ is —H, —$R^2$ is

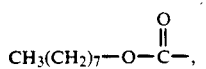

and —$R^3$ is —OH. The compound is synthesized as follows:

9-Fluorenylmethyl chloroformate (FMOC-chloride) is added to a solution of His-Gly-Gly and triethylamine in dichloromethane at 0° C., and the solution is stirred at room temperature for 1 hour. The volatiles are removed on a rotary evaporator and the residue is taken up in ethyl acetate and washed successively with 1M KHSO$_4$, water, saturated NaHCO$_3$ solution, and water. The ethyl acetate solution is dried over MgSO$_4$, filtered, and the solvent is removed on a rotary evaporator to form Nα-FMOC-His-Gly-Gly as a semisolid oil.

Phosgene (20% in toluene) is added to a solution of octanol and triethylamine in toluene at 0° C., then stirred at room temperature for 3 hours. This solution is then slowly added to a solution of Nα-FMOC-His-Gly-Gly and triethylamine in toluene and allowed to stir for 2 hours. The volatiles are removed on a rotary evaporator and the residue is taken up in ethyl acetate and washed successively with 1M KHSO$_4$, water, saturated NaHCO$_3$ solution, and water. The ethyl acetate solution is dried over MgSO$_4$, filtered, and the solvent is removed on a rotary evaporator to form Nα-FMOC-N-(im)-octyloxycarbonyl-His-Gly-Gly.

The FMOC-protecting group is removed with piperidine in dichloromethane at room temperature. The solvent is removed on a rotary evaporator and the residue is taken up in ethyl acetate and washed successively with 1M KHSO$_4$, water, saturated NaHCO$_3$ solution, and water. The ethyl acetate solution is dried over MgSO$_4$, filtered, and the solvent is removed on a rotary evaporator to form N-(im)-octyloxycarbonylhistidyl-glycyl-glycine as a semisolid oil.

Compositions for Regulating Hair Growth

One aspect of the present invention involves compositions for regulating hair growth comprising a safe and effective amount of a hair growth peptide. The amount of hair growth peptide can vary widely depending upon the needs of the subject. Preferred amounts of hair growth peptide in such compositions are from about 0.001% to about 20% by weight, more preferably from about 0.01% to about 10%, more preferably still from about 0.1% to about 5%, more preferably still from about 1% to about 2%.

The Carrier

The compositions of the present invention comprise a solid, semi-solid or liquid cosmetically and/or physiologically acceptable carrier to enable the hair growth peptide to be delivered to the desired target at an appropriate concentration. The carrier can itself be inert or it can possess physiological or pharmaceutical benefits of its own. The nature of the carrier will be dictated by the method chosen for administration of the composition. The method of administration of the hair growth peptide composition may range from internal methods such as injection to external topical methods.

A preferred method of administration of the hair growth peptide is by cutaneous injection. The carrier for facilitation of such administration would preferably comprise water or a saline solution, preferably an isotonic saline solution.

A more preferred method of administration of the hair growth peptide is by topical application. Topical application is preferably achieved with compositions in the forms of lotions, sprays, tonics, creams, shampoos, gels, mousse and the like.

Topical compositions of the present invention can be formulated as liquids, for example as a lotion, cream, shampoo, conditioner, gel, mousse or milk. Such liquid compositions may be formulated for use in conjunction with an applicator such as a roll-ball applicator, a tined applicator, a pad applicator, or a spray device such as an aerosol can containing propellant, or a container fitted with a pump to dispense the liquid product.

Alternatively, the compositions of the invention can be solid or semi-solid, for example sticks, creams or gels. Such solid or semi-solid compositions may be formulated for use in conjunction with a suitable applicator or simply a tube, or bottle, or as a liquid-impregnated fabric, such as a tissue wipe.

The selection of a carrier for this purpose presents a wide range of possibilities depending on the required product form of the composition. Suitable vehicles can be classified as described hereinafter.

The term "topical carrier" refers to substances which can act as diluents, dispersants, or solvents for the hair growth peptide which therefore ensure that it can be applied to and distributed evenly over the selected target at an appropriate concentration. The carrier is preferably one which can aid penetration of the hair growth peptide into the skin to reach the immediate environment of the hair follicle. Topical carriers useful in compositions of the subject invention can include water as a vehicle, and/or at least one cosmetically acceptable vehicle other than water. Carriers useful in topical compositions according to the invention may include liposomes, latex latices, microphages, and various forms of microencapsulation of the hair growth peptide.

Generally, the carrier is either organic in nature or an aqueous emulsion and capable of having the hair growth peptide dispersed or dissolved therein. The carrier may include pharmaceutically-acceptable emollients, skin penetration enhancers, coloring agents, fragrances, emulsifiers, thickening agents, and solvents.

A more detailed description of preferred topical composition follows:

1. Lotions

The lotions can comprise an effective amount (preferably from about 0.01% to about 20%, more preferably from about 0.1% to about 5%) of the hair growth peptide; from 1% to 50%, preferably from 3% to 15%, of an emollient; the balance being water, a $C_2$ or $C_3$ alcohol, or a mixture of water and the alcohol buffered from about pH 3 to about pH 9, preferably from about pH 6 to about pH 8. Several emollients are known. Examples of such emollients are as follows:

a. Hydrocarbon oils and waxes. Examples are mineral oil, petrolatum, paraffin, ceresin, ozokerite, microcrystalline wax, polyethylene, and perhydrosqualene.

b. Silicone oils, such as dimethylpolysiloxanes, methyl-phenylpolysiloxanes, water-soluble and alcohol-soluble silicaone-glycol copolymers and volatile silicone fluids such as cyclomethicone.

c. Triglyceride fats and oils such as those derived from vegetable, animal and marine sources. Examples include castor oil, safflower oil, cotton seed coil, corn oil, olive oil, cod liver oil, almond oil, avocado oil, palm oil, sesame oil, and soybean oil.

d. Acetoglyceride esters, such as acetylated monoglycerides.

e. Ethoxylated glycerides, such as ethoxylated glyceryl monostearate.

f. Alkyl esters of fatty acids having 10 to 20 carbon atoms. Methyl, isopropyl and butyl esters of fatty acids are useful herein. Examples include hexyl laurate, isohexyl laurate, isohexyl palmitate, isopropyl palmitate, isopropyl myristate, decyl oleate, isodecyl oleate, hexadecyl stearate, decyl stearate, isopropyl isostearate, diisopropyl adipate, dissohexyl adipate, dihexyldecyl adipate, diisopropyl sebacate, lauryl lactate, myristyl lactate, and cetyl lactate.

g. Alkenyl esters of fatty acids having 10 to 20 carbon atoms. Examples thereof include oleyl myristate, oleyl stearate, and oleyl oleate.

h. Fatty acids having 8 to 22 carbon atoms. Suitable examples include pelargonic, lauric, myristic, palmitic, stearic, isostearic, hydroxystearic, oleic, linoleic, ricinoleic, arachidonic, behenic, and erucic acids.

i. Fatty alcohols having 8 to 22 carbon atoms. Lauryl, myristyl, cetyl, hexadecyl, stearyl, isostearyl, hydroxystearyl, oleyl, ricinoleyl, behenyl, erucyl, and 2-octyl dodecyl alcohols are examples of satisfactory fatty alcohols.

j. Fatty alcohol ethers. Ethoxylated fatty alcohols of 8 to 20 carbon atoms include the lauryl, cetyl, stearyl, isostearyl, oleyl, and cholesterol alcohols having attached thereto from 1 to 50 ethylene oxide groups or 1 to 50 propylene oxide groups, or a mixture thereof.

k. Ether-esters such as fatty acid esters of ethoxylated fatty alcohols.

l. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

m. Polyhydric alcohols and polyether derivatives. Propylene glycol, glycerol (glycerine), dipropylene glycol, polypropylene glycol (M.W. 2000–4000), polyoxyethylene polyoxypropylene glycols, polyoxypropylene polyoxyethylene glycols, ethoxylated glycerol, propoxylated glycerol, sorbitol, ethoxylated sorbitol, kydroxypropyl sorbitol, polyethylene glycol (M.W. 200–5000), methoxy polyethylene glycols 350, tto, 750, 2000, 5000, poly[ethylene oxide] homopolymers (M.W. 100,000–5,000,000), polyalkylene glycols and derivatives, hexylene glycol (2-methyl-2-,4-pentanediol), 1,3-butylene glycol, 1,2,6-hexanetriol, ethohexadiol USP (2-ethyl-1,3-hexanediol) $C_{15}$–$C_{18}$ vicinal glycol, and polyoxypropylene derivatives of trimethylolpropane are examples thereof.

n. Polyhydric alcohol esters. Ethylene glycol mono- and di-fatty acid esters, diethylene glycol mono- and di-fatty acid esters, propylene glycol mono- and di-fatty acid esters, polypropylene glycol 2000 momooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

o. Wax esters such as beeswax, spermaceti, myristyl myristate, stearyl stearate.

p. Beeswax derivatives, e.g., polyoxyethylene sorbitol beeswax. These are reaction products of beeswax with ethoxylated sorbitol of varying ethylene oxide content, forming a mixture of ether-esters.

q. Vegetable waxes including carnauba and candelilla waxes.

r. Phospholipids such as lecithin and derivatives.

s. Sterols. Cholesterol, cholesterol fatty acid esters are examples thereof.

t. Amides such as fatty acid amides, ethoxylated fatty acid amide, solid fatty acid alkanolamides.

The lotions further preferably comprise from 1% to 10%, more preferably from 2% to 5%, of an emulsifier. The emulsifiers can be nonionic, anionic or cationic. Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxide, mono- and di-fatty acid esters of ethylene glycol wherein the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan and hydrophilic wax esters. Suitable anionic emulsifiers include the fatty acid soaps, e.g., sodium, potassium and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, an alkyl ethoxy ether sulfonates having 10 to 30 carbon atoms in the alkyl moiety. The alkyl ethoxy ether sulfonates contain from 1 to 50 ethylene oxide units. Satisfactory cationic emulsifiers are the quaternary ammonium, morpholinium and pryidinium compounds. Certain of the emollients described in preceding paragraphs also have emulsifying properties. When a lotion is formulated containing such an emollient, an additional emulsifier is not needed, though it can be included in the composition.

The balance of the lotion is water or a $C_2$-$C_3$ alcohol, or a mixture of water and the alcohol buffered from about pH 3 to about pH 9, preferably from about pH 6 to about pH 8. The lotions are formulated by simply admixing all of the components together. Preferably the compound of the present invention is dissolved in the mixture. Conventional optional components can be included. One such additive is a thickening agent at a level from 1% to 10% of the composition. Examples of suitable thickening agents include: cross-linked carboxypolymethylene polymers, ethyl cellulose, polyethylene glycols, gum tragacanth, gum kharaya, xanthan gums and bentonite, hydroxethyl cellulose, and hydroxypropyl cellulose.

2. Creams

The creams comprise an effective amount preferably from about 0.01% to about 20%, more preferably from about 0.1% to about 5%) of the hair growth peptide; from 5% to 50%, preferably from 10% to 25%, of an emollient; the balance being water buffered from about pH 3 to about pH 9, preferably from about pH 6 to about pH 8. The emollients described above can also be used in the cream compositions. Optionally the cream form contains a suitable emulsifier, as previously described. When an emulsifier is included, it is in the composition at a level from 3% to 50%, preferably from 5% to 20%.

3. Solutions

The solution form comprises an effective amount (preferably from about 0.01% to about 20%, more preferably from about 0.1% to about 5%, of the hair growth peptide; the balance being water and/or a suitable organic solvent buffered from about pH 3 to about pH 9, preferably from about pH 6 to about pH 8. Suitable organic materials useful as the solvent or a part of a solvent system are as follows: propylene glycol, glycerine, polyethylene glycol (M.W. 200-600), polypropylene glycol (M.W. 425-2025), glycerine, sorbitol esters, 1,2,6-hexanetriol, ethanol, isopropanol, diethyl tartrate, butanediol, and mixtures thereof. Such solvent systems can also contain water.

These compositions in solution form can be applied to the skin as is, or else can be formulated into an aerosol and applied to the skin as a spray-on. The aerosol compositions further comprise from 25% to 80%, preferably from 30% to 50%, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used at a level sufficient to expel the contents of the container.

4. Gels

Gel compositions can be formulated by simply admixing a suitable thickening agent to the previously described solution compositions. Examples of suitable thickening agents have been previously described with respect to the lotions.

The gel compositions comprise an effective amount (preferably from about 0.01% to about 20%, more preferably from about 0.1% to about 5%) of the hair growth peptide; from 5% to 75%, preferably from 10% to 50% of an organic solvent as previously described; from 0.5% to 20%, preferably from 1% to 10% of the thickening agent; the balance being water buffered from about pH 3 to about pH 9, preferably from about pH 6 to about pH 8.

5. Solids

Compositions of solid forms have use as stick-type compositions intended for application to the scalp or other parts of the body. Such compositions comprise an effective amount (preferably from about 0.01% to about 20%, more preferably from about 0.1% to about 5%) of the hair growth peptide, and from 50% to 98%, preferably from 60% to 90%, of the previously described emollients. This composition can further comprise from 1% to 20%, preferably from 5% to 15%, of a suitable thickening agent, and optionally emulsifiers and water. Thickening agents previously described with respect to lotions are suitable herein.

Penetration Enhancers

The presence of a penetration enhancer can potentates the benefit of the hair growth peptide by improving their delivery through the stratum corneum to its site of action in the immediate environment of the hair follicle.

The penetration enhancer can accordingly function in a variety of ways. It can, for example, improve the distribution of the hair growth peptide on the skin surface. Alteratively, it can increase its partition into the skin from the composition when applied topically, so aiding its passage to its site of action. Other mechanisms enhancing the benefit of the hair growth peptide may also be involved.

Examples of penetration enhancers include, but are not limited to: 1-dodecylazacycloheptan-2-one in combination with certain $C_3$-$C_4$ diols or a 1-substituted azacycloalkyl-2-One (see U.S. Pat. No. 4,557,934, Cooper, issued Dec. 10, 1985); a binary combination of a $C_3$-$C_4$ diol and a "cell-envelope disordering compound" (see U.S. Pat. No. 4,552,872, Cooper, Loomans and Fawzi, issued Nov. 12, 1985); a binary combination of N-(2-hydroxyethyl) pyrolidone and a "cell-envelope disordering compound" (see U.S. Pat. No. 4,537,776, Cooper, issued Aug. 27, 1985); a compound comprising aluryl alcohol, diisopropyl sebacate, dibutyl sebacate, dioctyl adipate, propylene glycol dipelargonate, butyl laurate, ethyl myristate, butyl myristate, isopropyl palmitate, oleyl alcohol, diethyl sebacate, dioctyl sebacate, dioctyl azelate, hexyl aurate, ethyl caprate, butyl stearate, isopyrpyl isostearate, 2-ethylhexyl pelargonate, butyl benzoate, benzyl benzoate, benzyl salicylate, dibutyl phthalate and/or ethyl laurate (see U.S. Pat. No. 4,299,826) Luedders, issued Nov. 10, 1981); a sugar ester in combination with a sulfoxide or phosphine oxide (see U.S. Pat. No. 4,150,114, Smith, issued Apr. 17, 1979; U.S. Pat. No. 4,148,917, Smith, issued Apr. 10, 1979; U.S. Pat. No. 4,148,887, Smith, issued Apr. 10, 1979; U.S. Pat. No. 4,148,874, Smith, issued Apr. 10, 1979; U.S. Pat. No. 4,148,893, Smith, issued Apr. 10, 1979; U.S. Pat. No. 4,130,667, Smith, issued Dec. 19, 1978; U.S. Pat. No. 4,046,886, Smith, issued Sep. 6, 1977; U.S. Pat. No. 3,952,099, Smith, issued Apr. 20, 1976; U.S. Pat. No. 3,896,238, Smith, issued Jul. 22, 1975); a carrier comprising aliphatic sulfoxides (See U.S. Pat. No. 3,953,599, MacMillan and Lyness, issued Apr. 27, 1976; U.S. Pat. No. 3,903,256. MacMillan and Lyness, issued Sep. 2, 1975; U.S. Pat. No. 3,839,566, MacMillan and Lyness, issued Oct. 1, 1974; U.S. Pat. No. 3,678,156, MacMillan and Lyness, issued Jul. 18, 1974; U.S. Pat. No. 3,678,156, MacMillan and Lyness, issued Jul. 18, 1972); a carrier comprising a binary combination of a $C_3$–$C_4$ diol or $C_3$–$C_4$ triol and a specific $C_{16}$ or $C_{18}$ alcohol polar lipid compound (See European Patent Application 249 397, Kasting, Smith, Massaro and Snyder, published Dec. 16, 1987); a carrier comprising a $C_3$–$C_4$ diol, diol ester or diol ether and a cell-enveloping disordering compound (See European Patent Application 095 813, Cooper, published Dec. 7, 1983; European Patent Application 043 738, Wickett, Cooper and Loomans, published Jan. 13, 1982); a carrier comprising a $C_6$–$C_{14}$ primary alkanol and a propane or butane diol (See European Patent Application 013 459, Wickett, Cooper and Loomans, published Jul. 23, 1980).

Iontophoresis

A further means for enhancing the activity of the hair growth peptides following topical application is the use of iontophoresis (i.e., the introduction of an active through the skin by the transfer of ions effected by means of the application of a direct electric current). A preferred iontophoretic device for this purpose comprises a pad of absorbent material, such as a nonwoven sheet or sponge, impregnated with a solution comprising the hair growth peptide, the pad carrying an electrode, for example in the form of a metallic sheet, through which an electric current can be passed, in order to enhance delivery of the growth factors to and through the epidermal layer of the skin.

Other Hair Growth Stimulants

The composition according to the invention can also optionally comprise other hair growth stimulants capable of functioning in different ways to enhance the benefit of the hair growth peptide. Examples of other substances with themselves possess the ability to regulate hair growth include, but are not limited to, minoxidil, retinoic acid, diazoxide, Iamin and its derivatives, anti-inflammatories, calcium channel blockers, anti-bacterials, nonionic surfactants, mucopolysaccharides, cellular growth factors, and antiandrogens.

Additional hair growth stimulants useful in compositions of the present invention comprising a hair growth peptide include the actives disclosed by the following, which are all incorporated herein by reference: U.S. Pat. No. 4,975,441, Gibson, issued Dec. 4, 1990; U.S. Pat. No. 4,761,401, Couchman, issued Aug. 2, 1988; U.S. Pat. No. 4,832,946, Green, issued May 23, 1989; European Patent Application 352 894, Bayley, published Jan. 31, 1990; European Patent Application 354 595, Couchman and Gibson, published Feb. 14, 1990; European Patent Application 415 598, Brawn, published Mar. 6, 1991; European Patent Application 375 388, Davis and Gibson, published Jun. 27, 1990; European Patent Application 397 519, Gibson and Scott, published Nov. 14, 1990; European Patent Application 398 669, Gibson, published Nov. 22, 1990; European Patent Application 403 238 Green, published Dec. 91, 1990; European Patent Application 334 586, Gibson, published Sep. 27, 1989; European Patent Application 334 585, Green, published Sep. 27, 1989; European Patent Application 342 054, Scott, published Nov. 15, 1989; European Patent Application 335 554, Green, published Oct. 4, 1989; European Patent Application 342 056, Scott, published Nov. 15, 1989; European Patent Application 348 184, Brawn, published Dec. 27, 1989; European Patent Application 297 428, Gibson, published Aug. 10, 1988; European Patent Application 295 092, Scott, published Dec. 14, 1988; European Patent Application 242 967, Gibson, published Oct. 28, 1987; European Patent Application 211 610, Couchman and Gibson, published Feb. 25, 1987; and European Patent Application 008 171, Mathur, Anaykar and Menon, published Feb. 20, 1980.

Other Ingredients

The composition according to the invention can contain ingredients other than those already mentioned, depending on the form of the intended product. It is, for example, possible to include antiseptics, preservatives, antioxidants, emulsifiers, coloring agents and surfactants.

The composition according to the invention can also be employed as a vehicle for a wide variety of cosmetically or pharmaceutically active ingredients, particularly ingredients which have some beneficial effect when applied to the skin other than the promotion of hair growth.

The composition according to the invention can also optionally comprise a perfume in an amount sufficient to make the composition acceptable to the consumer and pleasant to use. Usually, the perfume will form from 0.01% to 0.1% by weight of the composition.

Use of Compositions to Induce, Maintain or Increase Hair Growth

The invention also provides for use of the hair growth peptide for regulating hair growth. In one embodiment, the present invention provides for the use of the hair growth active for preventing hair loss. Such prophylactic application is particularly useful to individuals who have a family history of baldness. In another embodiments, the present invention provides for the use of the hair growth active for stimulating new hair growth. The following methods of use may be used to regulate hair growth.

The compositions according to the invention are preferably intended for application by cutaneous injection. The amount of the composition and the frequency of cutaneous injection can vary widely, depending on personal needs. As an example of application by cutaneous injection, it is suggested that a composition suitable for cutaneous injection comprising the hair growth peptide be cutaneously injected preferably from about once per day to about once every six months, more preferably from about once per week to about twice per month. The composition for cutaneous injection will preferably administer from about 0.01 to about 1.0 mg of the hair growth peptide per $cm^2$ skin receiving cutaneous injection, more preferably from about 0.020 to about 0.500 $mg/cm^2$, more preferably still from about 0.050 to about 0.100 $mg/cm^2$. The period of injections would preferably be over a period of from about one month to about ten years, more preferably from about three months to about two years, more preferably still from about six months to about one year, thereby resulting in regulation of hair growth.

A more preferred method of applying the compositions according to the present invention involves topical application to the scalp of a human subject to regulate hair growth, particularly where the scalp is already bald or balding. The amount of the composition and the frequency of application to the hair and/or scalp can vary widely, depending on personal needs, but it is suggested as an example that topical application preferably range from about 1 to about 10 times daily, more preferably from about 1 to about 6 times daily, more preferably still from about 1 to about 3 times daily, and most preferably about once per day. The composition for topical application will preferably contain from about 0.005 to about 5.0 mg of the hair growth peptide per $cm^2$ skin receiving the topical composition, more preferably from about 0.1 to about 2.5 $mg/cm^2$, more preferably still from about 0.25 to about 1.0 $mg/cm^2$. The period of topical application may be over the subject's life, but would preferably be over a period of from about one month to about ten years, more preferably from about three months to about two years, more preferably still from about six months to about one year, thereby resulting in regulation of hair growth.

Example VII

A topical composition comprising a hair growth peptide of the present invention is prepared by combining the following components utilizing conventional mixing techniques.

| Component | Percent by Weight of Compositions |
| --- | --- |
| Histidyl-glycyl-glycine | 1 |
| Propylene Glycol | 30 |
| Glycerine | 3 |
| TRis Buffer (pH 8) | 66 |

1000 mg of the composition per 100 $cm^2$ skin is topically applied twice per day for one year to a subject resulting in new hair growth.

Example VIII

A topical composition comprising a hair growth peptide of the present invention is prepared by combining the following components utilizing conventional mixing techniques.

| Component | Percent by Weight of Compositions |
| --- | --- |
| Histidyl-glycyl-glycine n-octyl ester | 0.5 |
| Propylene Glycol | 30.0 |
| Propylene Glycol Laurate | 1.0 |
| Isopropanol | 20.0 |
| TRis Buffer (pH 8) | 48.5 |

5 mg of the composition per 100 $cm^2$ skin is topically applied once per day for 6 months to a subject resulting in a prevention of hair loss.

Example IX

An injectable composition comprising a hair growth peptide of the present invention is prepared by combining the following components utilizing conventional mixing techniques.

| Component | Percent by Weight of Compositions |
| --- | --- |
| N-Histidyl-glycyl-glycine n-octyl amide | 0.05 |
| Saline | 99.90 |

0.1 cc of the composition per $cm^2$ skin is injected at the site of desired hair regulation once every two weeks for six months to a subject resulting in new hair growth.

Evaluation of Efficacy of the Hair Growth Peptides Using the C3H Mouse Model The effect of the compounds of the present invention on hair growth is assessed using male C3H mice (Harlan Sprague Dawley, Inc., Indianapolis, Ind.) as an animal model. The mice are 52 days old at the time of first does. They are individually housed in "shoe box" cages (Scientific Products, Chicago, Ill.). Ten mice are used per test group.

Not more than four hours before treatment, the animals are anesthetized with an intraperitoneal mixture of acepromazine maleate (1.6 mg/kg), xylazine (4.8 mg/kg) and ketamine hydrochloride (64 mg/kg) dosed in a saline vehicle in a total volume of 0.2 ml per 25 g mouse. The entire back of the animal is clipped closely with a small animal clipper (Wahl model 8900, Wahl Clipper Corp., Sterling, Ill.). The animals are then fitted with small collars to minimize ingestion of topically applied product. Animals are weighed and allowed to recover from anesthesia prior to treatment.

For topical studies, 0.2 ml of the test compound is applied to the shaved area with a 1.0 ml syringe (without needle). The solution is spread evenly with light stroking with the syringe, and the animal is returned to its cage. In topical studies, the animals are dosed 5 consecutive days per week for four weeks.

For intradermal studies, 100 ul of the test compound is injected into both the upper and lower regions of the shaved area along the spine. A 1.0 ml (or smaller) syringe with a 30 gauge needle is used. For intradermal studies, animals receive the two intradermal injections only on Day 0.

For topical studies, the animals are photographed for assessment of hair growth on Days 14, 16, 18 and 25 after the start of dosing (the first dose having occurred on Day 0).

For intradermal studies, animals are photographed on Days 14, 21 and 28.

On days of photography, the animals are photographed prior to dosing. Photography is accomplished using a 35 mm camera. Slides are made, and computer planimetry is used to circumscribe the total shaved area, the area demonstrating dark pigmented skin ("anagen skin"), and the area demonstrating visible hair growth. Results are expressed as the percent of shaved area responding with anagen skin, and the percent of shaved area responding with hair growth.

A positive response, i.e., an increase of greater than 10% over control, indicates the potential of the test compound to regulate hair growth. Accordingly, when hair growth peptides as herein defined, are assessed either individually or in combination as a test compound in the C3H Mouse Model, an increase over control of at least 10%, preferably 40%, more preferably 70%, after four weeks treatment will be obtained. Usually the 10% minimum value will be attained well before the end of this four week period.

Example X

Topical treatment with a composition according to the invention was found to stimulate hair growth. In this example, the effect of topical application of His-Gly-Gly is shown. The formulations tested were the following:

| Vehicle (control) | Tris buffer/propylene glycol/glycerine (67/30/3, w/w/w, pH = 8.0) |
|---|---|
| His-Gly-Gly | 1.0% in 67/30/3 vehicle |

The following results show the mean percent of shaved area that is covered with hair at Day 25 (after 4 weeks of treatment). Values represent the means values for a group of 10 mice.

| Vehicle (control) | 22.6 |
|---|---|
| His-Gly-Gly | 44.3 |

These results indicate that a 96% increase in hair growth was obtained in this experiment.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

What is claimed is:

1. A composition for regulating hair growth comprising
   a) from about 0.001% to about 20% His-Gly-Gly; and
   b) a pharmaceutically acceptable carrier.

2. The composition of claim 1 wherein the composition comprises from about 0.01% to about 10% His-Gly-Gly.

3. The composition of claim 2 wherein the composition comprises from about 0.1% to about 5% His-Gly-Gly.

4. The composition of claim 3 wherein the composition comprises from about 1% to about 2% His-Gly-Gly.

5. The composition of any of claims 1, 2, 3 and 4 wherein the pharmaceutically-acceptable carrier is a topical carrier.

6. The composition of any of claims 1, 2, 3 and 4 wherein the composition additionally comprises an emollient.

7. The composition of any of claims 1, 2, 3 and 4 wherein the pharmaceutically-acceptable carrier is an injectable carrier.

* * * * *

UNITED STATES PATENT AND TRADEMARK OFFICE
CERTIFICATE OF CORRECTION

PATENT NO. : 5,252,559

DATED : October 12, 1993

INVENTOR(S) : Kronholm et al.

It is certified that error appears in the above-identified patent and that said Letters Patent is hereby corrected as shown below:

Column 10, line 16, "kydroxypropyl" should read --hydroxypropyl--.
Column 13, line 14  "U.S. Pat. No. 3,678,156, MacMillan and Lyness, issued
        and 15    Jul. 18, 1972;" should be deleted.
Column 3, line 33, "reason sable" should read --reasonable--.
Column 6, line 10, "ether" should read --ester--.
Column 9, line 32, "coil" should read --oil--.
Column 10, line 49, "amide" should read --amides--.
Column 11, line 31, "preferably" should read--(preferably--.
Column 13, line 21, "enveloping" should read --envelope--.
Column 14, line 4, "91" should read --19--.
Column 16, line 19, "does" should read--dose--.

Signed and Sealed this

Thirteenth Day of September, 1994

Attest:

BRUCE LEHMAN

*Attesting Officer*    *Commissioner of Patents and Trademarks*